United States Patent [19]

Brandt

[11] Patent Number: 4,699,993

[45] Date of Patent: Oct. 13, 1987

[54] PERFLUOROALKYLNAPHTHALENE COMPOUNDS

[75] Inventor: Vernon O. Brandt, Baton Rouge, La.

[73] Assignee: Ethyl Corporation, Richmond, Va.

[21] Appl. No.: 808,000

[22] Filed: Dec. 12, 1985

[51] Int. Cl.$^4$ ............................................. C07C 121/62
[52] U.S. Cl. .................................... 558/423; 558/424; 558/425
[58] Field of Search ......................... 558/423, 424, 425

[56] References Cited

U.S. PATENT DOCUMENTS

| | | | |
|---|---|---|---|
| 3,408,411 | 10/1968 | Conrad et al. | 260/646 |
| 4,439,617 | 3/1984 | Sestanj et al. | 560/39 |
| 4,590,010 | 5/1986 | Ramachandran et al. | 558/341 |
| 4,604,406 | 8/1986 | Bellini et al. | 514/562 |

OTHER PUBLICATIONS

McLoughlin et al., *Tetrahedron*, vol. 25, pp. 5921–5940 (1969).
Kobayashi et al., *Tetrahedron Letters*, pp. 4071–4072 (1979).
Gassman et al., *Tetrahedron Letters*, vol. 26, No. 43, pp. 5243–5246 (1985).

*Primary Examiner*—Dolph H. Torrence
*Attorney, Agent, or Firm*—Donald L. Johnson; John F. Sieberth; Patricia J. Hogan

[57] ABSTRACT

Novel compounds having greatest interest as biologically-active materials for the treatment of diabetic complications in mammals, or intermediates for such materials, are perfluoroalkyl compounds corresponding to the formula:

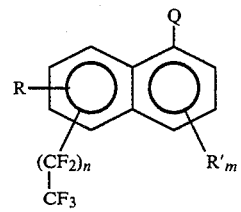

wherein R and R' are independently selected from chloro, fluoro, nitro, hydroxy, and alkyl and alkoxy substituents containing 1–6 carbons; Q is —CN, —COOL, —COX, or —CTN(R")CH$_2$COOL; L is hydrogen, alkali metal, or saturated hydrocarbyl; X is halo; T is oxygen or sulfur; R" is an alkyl group containing 1–6 carbons; m is 0 or 1; and n is an integer of at least one.

4 Claims, No Drawings

PERFLUOROALKYLNAPHTHALENE COMPOUNDS

FIELD OF THE INVENTION

This invention relates to perfluoroalkylnaphthalene compounds.

BACKGROUND

As disclosed in McLoughlin et al., *Tetrahedron*, Vol. 25, pp. 5921–5940, 1969, Kobayashi et al., *Tetrahedron Letters*, No. 42, pp. 4071–4072, 1979, Gassman et al., *Tetrahedron Letters*, Vol. 26, No. 43, pp. 5243–5246, 1985, and U.S. Pat. Nos. 3,408,411 (McLoughlin et al.) and 4,439,617 (Sestanj et al.), it is known that perfluoroalkylaromatic compounds are apt to be useful as biologically-active compounds, surfactants, coatings, sealants, dyestuffs, alkyd-type resins, etc.; and they can be prepared in various ways.

SUMMARY OF THE INVENTION

An object of this invention is to provide novel perfluoroalkylnaphthalene compounds.

Another object is to provide such compounds wherein the perfluoroalkyl groups contain at least two carbons.

A further object is to prepare such compounds having biological activity.

These and other objects are attained by the provision of compounds corresponding to the formula:

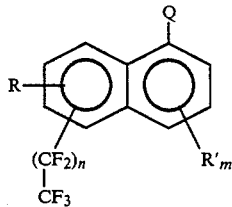

wherein R and R' are independently selected from chloro, fluoro, nitro, hydroxy, and alkyl and alkoxy substituents containing 1–6 carbons; Q is —CN, —COOL, —COX, or —CTN(R'')CH$_2$COOL; L is hydrogen, alkali metal, or saturated hydrocarbyl; X is halo; T is oxygen or sulfur; R'' is an alkyl group containing 1–6 carbons; m is 0 or 1; and n is an integer of at least one.

DETAILED DESCRIPTION

The compounds of the invention are substituted naphthalenes that can be prepared in any suitable manner. In fact, although they have not previously been identified or contemplated as potentially useful, it is believed that some of them have been inadvertently formed in the past as by-products of certain reactions for preparing their trifluoromethyl homologs. However, because of the very small yield of higher perfluoroalkyl compounds apt to be obtained in reactions designed to prepare trifluoromethyl compounds, it is generally preferred to synthesize the compounds of the invention by procedures such as those described below.

PREPARATION OF (PERFLUOROALKYL)CYANONAPHTHALENES

Compounds of the above formula wherein Q is cyano can be prepared by reacting the appropriate potassium perfluoroalkanoate with the appropriate halocyanonaphthalene corresponding to the formula:

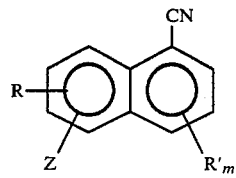

wherein R and R' are independently selected from chloro, fluoro, nitro, hydroxy, and alkyl and alkoxy substituents containing 1–6 carbons; Z is bromo or iodo; and m is 0 or 1, at a suitable temperature, conveniently at reflux temperatures, in the presence of cuprous iodide and a dipolar aprotic solvent, such as N-methylpyrrolidone, N,N-dimethylformamide, N,N-dimethylacetamide, hexamethylphosphoric triamide, etc. Ordinarily, the temperature is in the range of about 140°–160° C., the amount of cuprous iodide employed is about 0.5–5 mols per mol of halocyanonaphthalene, and the solvent is used in solvent amounts, e.g., an amount such as to provide an organic solids concentration of up to about 15%.

Since there does not appear to be any maximum to the number of CF$_2$ groups that can desirably be incorporated into the substituted naphthalene molecule, the potassium perfluoroalkanoate employed in the reaction may be any compound corresponding to the formula KOOC(CF$_2$)$_n$CF$_3$ wherein n is an integer of at least one, and it is generally the salt which contains the same number of CF$_2$ groups as is desired in the product. However, because of cost and availability factors, as well as the fact that the reaction typically permits the formation of at least some (perfluoroalkyl)cyanonaphthalene containing more CF$_2$ groups in the substituent than are present in the perfluoroalkanoate, the preferred reactants are those containing about 1–16 CF$_2$ groups, such as potassium pentafluoropropionate, heptafluorobutyrate, nonafluorovalerate, tridecafluoroheptanoate, pentadecafluorooctanoate, heptadecafluorononanoate, nondecafluorodecanoate, etc. The amount of perfluoroalkanoate used is ordinarily about 1–20, most commonly about 1.5–3, mols per mol of halocyanonaphthalene.

The halocyanonaphthalenes that may be employed in the reaction are preferably compounds wherein m is 0, Z is in the 5-position, and R is an alkyl or alkoxy substituent in the 6-position. When the R and R' substituents are alkyl or alkoxy, they are generally straight-chain groups of 1–3 carbons or branched-chain groups of 3 or 4 carbons, such as methyl, ethyl, propyl, 1-methylethyl, butyl, 2-methylpropyl, 1,1-dimethylethyl, the corresponding alkoxy groups, etc., although, as indicated above, larger groups such as hexyl and hexanoxy are also utilizable. Particularly preferred halonaphthalenes are 5-bromo-6-methoxy-1-cyanonaphthalene and 5-iodo-6-methoxy-1-cyanonaphthalene.

The halocyanonaphthalenes used as starting materials in this reaction are compounds that can be prepared by cyanating the appropriately substituted tetralone, e.g., 6-methoxytetralone, to form the appropriately substituted 1-cyano-3,4-dihydronaphthalene, e.g., 6-methoxy-1-cyano-3,4-dihydronaphthalene, aromatizing the product in any suitable manner, and brominating or iodinating the resultant substituted 1-cyanonaphthalene by known techniques.

PREPARATION OF PERFLUOROALKYLNAPHTHOATE ESTERS

Compounds of the invention wherein Q is an ester group can be prepared in essentially the same manner as the (perfluoroalkyl)cynaonaphthalenes except for the use as the starting material of a halonaphthoate corresponding to the formula:

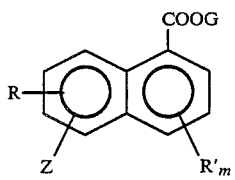

wherein R and R' are independently selected from chloro, fluoro, nitro, hydroxy, and alkyl and alkoxy substituents containing 1–6 carbons; G is a saturated hydrocarbyl group (i.e., a hydrocarbyl group that is free of aliphatic unsaturation), Z is bromo or iodo; and m is 0 or 1. These compounds are already known and are generally esters wherein G is an alkyl, cycloalkyl, aryl, alkaryl, or aralkyl group containing 1–10 carbons, especially methyl, ethyl, propyl, cyclohexyl, phenyl, tolyl, benzyl, etc. As in the case of the corresponding nitriles, the esters are preferably compounds wherein m is 0, Z is in the 5-position, and R is an alkyl or alkoxy substituent in the 6-position.

PREPARATION OF PERFLUOROALKYLNAPHTHOIC ACIDS AND SALTS

Compounds of the invention wherein Q is an acid or alkali metal salt group may be prepared by using conventional techniques to hydrolyze the corresponding (perfluoroalkyl)cyanonaphthalenes or perfluoroalkylnaphthoate esters in the presence of a base such as sodium or potassium hydroxide.

ADDITIONAL SYNTHESES

The remaining compounds of the invention can be prepared by procedures analogous to those employed for the preparation of the trifluoromethyl homologs by Sestanj et al., the teachings of which are incorporated herein in toto by reference. Thus, (1) a perfluoroalkylnaphthoic acid of the invention can be halogenated, e.g., by reaction with thionyl chloride, to form the corresponding acid halide, (2) the acid halide may be reacted with a saturated hydrocarbyl ester of an acid corresponding to the formula:

R"NHCH2COOH (e.g., methyl, ethyl, propyl, cyclohexyl, phenyl, tolyl, or benzyl sarcosinate, the corresponding esters of aminoacetic acids having N-ethyl, N-propyl, etc., substituents) to form an amide corresponding to the formula:

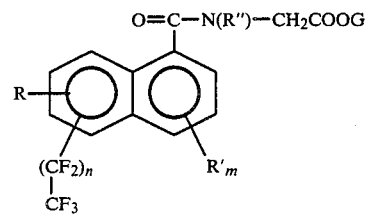

(3) the amide may be saponified to form the corresponding salt, then hydrolyzed to the corresponding acid, and then thiated, e.g., with phosphorus pentasulfide or the like, to form a thioamide corresponding to the formula:

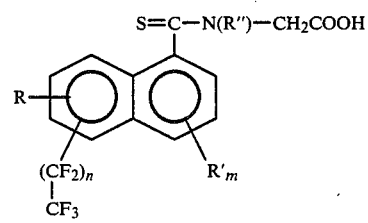

or (4) the thioamide may be prepared by thiating the amide and then subjecting the product to the saponification and hydrolysis steps.

The invention is advantageous in that it provides new perfluoroalkyl compounds having the potential for utility in various applications, such as surfactants, coatings, sealants, resins, dyestuffs, etc. but having greatest interest as biologically-active materials or precursors therefor, especially as materials to be used in preventing or relieving diabetic complications in a diabetic mammal. Because of their longer perfluoroalkyl chains, they have greater lipophilicity than the corresponding trifluoromethyl compounds—a factor that alters their in vivo absorption and transport rates.

The following examples are given to illustrate the invention and are not intended as a limitation thereof.

EXAMPLE I

A suitable reaction vessel was charged with 8.1 g of 6-methoxy-5-bromo-1-cyanonaphthalene, 11.8 g of CuI, 35 ml of toluene, and 55 ml of N,N-dimethylformamide. The reaction mixture was heated to 165° C. with concurrent azeotropic removal at toluene/water (25 ml) and then maintained at 155° C. when 11.8 g of potassium pentafluoropropionate was added. The reaction was monitored by VPC. After five hours no starting material was detected and the reaction mixture was poured into 150 ml of water and 125 ml of methylene chloride. The two phases were filtered, after which the organic layer was separated, washed with brine, and concentrated in vacuo to provide a crude 6-methoxy-5-pentafluoroethyl-1-cyanonaphthalene (6-MPCN) having a purity of greater than 95%.

EXAMPLE II

The crude 6-MPCN product of Example I was dissolved in 135 ml of methanol and 40 ml of a potassium hydroxide solution (4.5 g of KOH in 40 ml of water) and heated to 125° C./70 psi for seven hours. The reaction mixture was then worked up and acidified to yield 6.6 g of 6-methoxy-5-pentafluoroethyl-1-naphthoic acid.

It is obvious that many variations may be made in the products and processes set forth above without departing from the spirit and scope of this invention.

What is claimed is:

1. A compound corresponding to the formula:

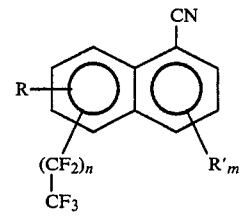

wherein R and R' are independently selected from chloro, fluoro, nitro, hydroxy, and alkyl and alkoxy substituents containing 1–6 carbons; m is 0 or 1; and n is an integer of at least one.

2. The compound of claim 1 wherein m is 0, the $(CF_2)_nCF_3$ substituent is in the 5-position, and R is an alkyl or alkoxy substituent in the 6-position.

3. The compound of claim 1 wherein n is 1–16.

4. The compound of claim 1 which is a 6-methoxy-5-perfluoroalkyl-1-cyanonaphthalene.

* * * * *